United States Patent [19]

Neustadt

[11] 4,058,612

[45] Nov. 15, 1977

[54] 6-(POLYHALOISOPROPYL)QUINAZOLINE-2,4-DIONES

[75] Inventor: Bernard R. Neustadt, West Orange, N.J.

[73] Assignee: Schering Corporation, Kenilworth, N.J.

[21] Appl. No.: 688,219

[22] Filed: May 20, 1976

Related U.S. Application Data

[63] Continuation-in-part of Ser. No. 528,603, Dec. 2, 1974, abandoned.

[30] Foreign Application Priority Data

Nov. 21, 1975 Switzerland ............... 15164/75

[51] Int. Cl.$^2$ ............... A61K 31/505; C07D 239/96
[52] U.S. Cl. ............... 424/251; 260/260; 260/553 A; 560/34

[58] Field of Search ............... 260/251 QA, 260; 424/251

[56] References Cited

U.S. PATENT DOCUMENTS

| 3,794,643 | 2/1974 | Yabuuchi et al. ............... 260/260 |
| 3,879,393 | 4/1975 | Havera ............... 424/251 |

*Primary Examiner*—Paul M. Coughlan, Jr.
*Attorney, Agent, or Firm*—Barbara L. Cowley Renda; Stephen B. Coan; Bruce M. Eisen

[57] ABSTRACT

Novel 6-(polyhaloisopropyl)quinazoline-2,4-diones, preparable from polyhaloisopropylarylureas, are disclosed herein. These compounds display potent hypotensive activity and are thus useful in the treatment of mammalian hypertension.

12 Claims, No Drawings

6-(POLYHALOISOPROPYL)QUINAZOLINE-2,4-DIONES

This application is a continuation-in-part of my co-pending application Ser. No. 528,603, filed Dec. 2, 1974, now abandoned, which is hereby incorporated by reference.

This invention relates to novel 6-(polyhaloisopropyl)-quinazoline-2,4-diones which are useful agents in the treatment of mammalian hypertension. More particularly, this invention relates to compounds of the formula:

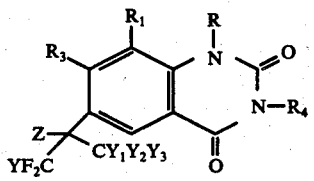

wherein
  $R_4$ is a methyl, ethyl, 2-chloroethyl or 2-bromoethyl group;
  $R_1$ and $R_3$ are independently hydrogen, fluorine, chlorine, bromine, lower alkyl, or lower alkoxy;
  Y, $Y_1$, $Y_2$ and $Y_3$ are independently hydrogen, fluorine or chlorine;
  Z is hydrogen, chlorine, hydroxy or lower alkanoyloxy; and
  R is hydrogen or alkyl having 1 to 4 carbon atoms.

The lower alkoxy groups referred to above contain 1 to 6 carbon atoms and are exemplified by such groups as methoxy, ethoxy, isopropoxy and the like. The lower alkanoyloxy groups contain 2 to 6 carbon atoms and are exemplified by acetoxy, propionyloxy and the like.

The lower alkyl groups likewise contain 1 to 6 carbon atoms and are represented by methyl, ethyl, propyl, butyl, pentyl, hexyl and the corresponding branched-chain isomers thereof.

Within the scope of formula I there are certain preferential embodiments. R is preferably hydrogen or an alkyl group containing 1 to 4 carbon atoms. $R_1$ and $R_3$ are preferably hydrogen or a lower alkyl group. Z is preferably a hydroxy group.

Particularly preferred compounds of this invention are 3-ethyl-6-(hexafluoro-2-hydroxy-2-propyl)quinazoline-2,4-dione and 6-(chloro-2-hydroxypentafluoro-2-propyl)-3-ethyl-1-methylquinazoline-2,4-dione.

The compounds of formula I are prepared as outlined in Scheme A:

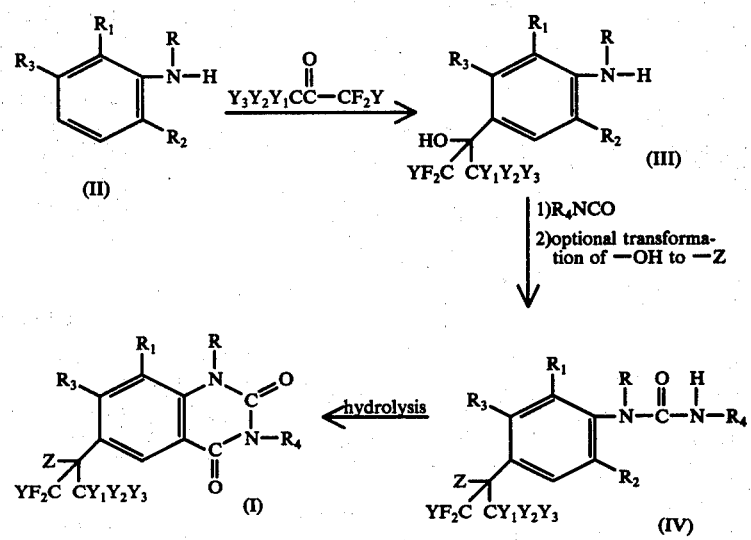

Scheme A wherein R, $R_1$, $R_3$, $R_4$, Y, $Y_1$, $Y_2$ and $Y_3$ are as hereinbefore defined and $R_2$ is a lower alkoxycarbonyl group having 1 to 6 carbon atoms in the alkoxy portion.

As shown in Scheme A, a 2-(lower alkoxycarbonyl)aniline of formula I is first reacted with a polyhalo ketone or hydrate thereof to form the corresponding 2-alkoxycarbonyl-4-(polyhalo-2-hydroxy-2-propyl)aniline of formula III. The intermediate of formula III is then contacted with the appropriate isocyanate to form the urea of formula IV. Hydrolysis of the urea of formula IV in an aqueous medium using either acid or base closes the ring to form the desired quinazoline-2,4-dione of formula I. Preferred bases for effecting this hydrolysis are alkali metal hydroxides such as sodium and potassium hydroxide.

The compounds of formula I wherein Z is other than hydroxy are prepared by transformation of the intermediate urea of formula IV. The compounds wherein Z is a chlorine atom are typically prepared by contacting the urea of formula IV wherein Z is hydroxy with a suitable chlorinating agent, e.g., thionyl chloride. For instance, N-ethyl-N'-[4-(hexafluoro-2-hydroxy-2-propyl)-2-(ethoxycarbonyl)phenyl]urea is conveniently converted to N-ethyl-N'-[4-(2-chloro-hexafluoro-2-propyl)-2-(ethoxycarbonyl)phenyl]urea in this manner.

The compounds wherein Z is hydrogen are obtained by catalytic reduction of the corresponding compound wherein Z is chlorine. Thus, N-ethyl-N'-[4-(2-chloro-hexafluoro-2-propyl)-2-(ethoxycarbonyl)phenyl]urea may be converted to N-ethyl-N'-[4-(1,1,1,3,3,3-hexafluoro-2-propyl)-2-(ethoxycarbonyl)phenyl] urea by this method.

The urea of formula IV having the desired Z group is then converted by hydrolysis to the quinazoline-2,4-dione as described hereinbefore. My copending patent application Ser. No. 683,104 further details the preparation of the ureas of formula IV.

Reaction of the compounds of formula I wherein Z is hydroxy with the appropriate acid chloride affords the corresponding alkanoyloxy derivative. For instance, reaction of 3-ethyl-6-(hexafluoro-2-hydroxy-2-propyl)-quinazoline-2,4-dione with acetyl chloride yields 3-ethyl-6-(2-acetoxyhexafluoro-2-propyl)quinazoline-2,4-dione.

An alternate process for the preparation of the quinazoline-2,4-diones of formula I involves the N-alkylation of a compound of the formula:

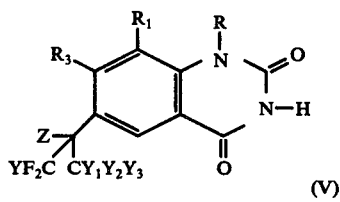

wherein R, $R_1$, $R_3$, Z, Y, $Y_1$, $Y_2$ and $Y_3$ are as hereinbefore defined with the appropriate alkyl halide or alkyl sulfonate ester in the presence of a strong base and in an organic solvent. A preferred base for this reaction is sodium hydride while preferred solvents are dimethylformamide or dimethylsulfoxide.

The compounds of the present invention have been found to exhibit useful and potent antihypertensive activity. Further, the compounds of this invention exhibit this antihypertensive effect with minimal undesirable side effects and/or tolerance. Based upon laboratory tests, the effective dose ($ED_{50}$) of the active ingredient in the compositions of the present invention will typically be within the range of from 1 to 50 mg/kg, preferably 10-20, of mammalian weight administered orally.

The required daily dosage may be administered in single or divided dosages. The exact dose to be administered is dependent upon where the particular compound lies within the above quoted range, as well as upon the age and weight of the subject mammal.

The compounds are preferentially administered orally. In any event, a suitable pharmaceutical carrier is employed, with the carrier selected according to the physical properties of the compound in the pharmaceutical composition. The carrier should not react chemically with the compound to be administered. The preparations containing the active ingredients may typically be in the form of tablets, capsules, syrups, elixirs, suspensions and the like.

In treating certain patients with the compounds of this invention it may be desirable to include other pharmaceutically active ingredients in the same dosage unit. For example, in treating patients in whom salt and water retention is a problem, effective amounts of conventional diuretics can be incorporated, such as the thiazide diuretics, e.g., hydrochlorothiazide or trichloromethiazide. Similarly, in treating patients in whom tachycardia might be a problem, an effective amount of a pharmaceutically acceptable beta-blocking agent can be included e.g., propranolol. The dosage unit may even contain a combination of a compound of this invention, e.g., 3-ethyl-6-(hexafluoro-2-hydroxy-2-propyl)quinazoline-2,4-dione, a diuretic, e.g., hydrochlorothiazide, and a beta-blocker, e.g., propranolol.

The following examples describe in detail compounds and compositions illustrative of the present invention. It will be apparent to those skilled in the art that many modifications, both of materials and methods, may be practiced without departing from the purpose and intent of this disclosure.

EXAMPLE 1

Ethyl-5-(hexafluoro-2-hydroxy-2-propyl)anthranilate

Combine 16.5 g (0.1 mole) of ethyl anthranilate with 38.6 g (0.20 mole) of hexafluoroacetone sesquihydrate and reflux 24 hours. Add 19.3 g (0.1 mole) of hexafluoroacetone sesquihydrate to the reaction mixture and reflux for another 24 hours. Distill off the excess hexafluoroacetone hydrate in vacuo. Wash the residual solid with hexane and obtain 25 g of pink solid. Recrystallize from ethanol and $H_2O$ to obtain 20 g of ethyl-5-(hexafluoro-2-hydroxy-2-propyl)anthranilate as a pink solid; m.p. 115°-117° C.

EXAMPLE 2

N-ethyl-N'-[4-(hexafluoro-2-hydroxy-2-propyl)-2-(ethoxycarbonyl)phenyl]urea

Combine 4.3 g (13 mmole) of ethyl 5-(hexafluoro-2-hydroxy-2-propyl)anthranilate from the preceeding example, and 1.8 g (26 mmole) of ethyl isocyanate with 20 ml of $Et_2O$. Reflux for 5 days. Each day add another 1.8 g portion of ethyl isocyanate. Concentrate the reaction mixture to obtain 5.5 g of a white solid. Recrystallize from $Et_2O$-hexane to obtain 4.5 g of N-ethyl-N'-[4-(hexafluoro-2-hydroxy-2-propyl)-2-(ethoxycarbonyl)-phenyl]urea as a white solid; m.p. 144°-146° C.

EXAMPLE 3

3-ethyl-6-(hexafluoro-2-hydroxy-2-propyl)quinazoline-2,4-dione

Combine 4.02 g (10 mmole) of N-ethyl-N'-[4-(hexafluoro-2-hydroxy-2-propyl)-2-(ethoxycarbonyl)-phenyl]urea with 21 ml (20 mmole) 1N NaOH and stir for 1 minute. Acidify the reaction with 1N HCl and extract with 100 ml of $Et_2O$. Dry and concentrate the extract to obtain 3.5 g of white solid. Recrystallize from $Et_2O$-hexane to obtain 2.5 g of white solid 3-ethyl-6-(hexafluoro-2-hydroxy-2-propyl)quinazoline-2,4-dione; m.p. 268°-270° C.

EXAMPLE 4

Repetition of the procedures detailed in the above examples using the appropriate starting materials affords the following compounds of this invention:

6-(1,3-dichloro-2-hydroxytetrafluoro-2-propyl)-3-ethyl-quinazoline-2,4-dione;
3-ethyl-6-(hexafluoro-2-hydroxy-2-propyl)-1-methyl-quinazoline-2,4-dione;
6-(chloro-2-hydroxypentafluoro-2-propyl)-3-ethyl-1-methylquinazoline-2,4-dione;
3-ethyl-6-(hexafluoro-2-hydroxy-2-propyl)quinazoline-2,4-dione;
3-bromoethyl-6-(hexafluoro-2-hydroxy-2-propyl)-quinazoline-2,4-dione;
7-methyl-6-(hexafluoro-2-hydroxy-2-propyl)-3-ethyl-quinazoline-2,4-dione;
8-propyl-6-(hexafluoro-2-hydroxy-2-propyl)-3-ethyl-quinazoline-2,4-dione;
7-chloro-6-(hexafluoro-2-hydroxy-2-propyl)-3-ethyl-quinazoline-2,4-dione;

8-methoxy-6-(hexafluoro-2-hydroxy-2-propyl)-3-ethyl-quinazoline-2,4-dione.

EXAMPLE 5

| Tablet Formulations | |
|---|---|
| Formulation I | Milligrams per Tablet |
| 3-ethyl-6-(hexafluoro-2-hydroxy-2-propyl)-1-methylquinazoline-2,4-dione | 50 |
| Lactose, direct compression grade | 173 |
| Microcrystalline cellulose | 30 |
| Sodium Lauryl Sulfate | 20 |
| Corn starch | 25 |
| Magnesium stearate | 2 |
| | 300 |

Mix together the stated active ingredient, lactose, microcrystalline cellulose, sodium lauryl sulfate, and corn starch. Pass through a No. 40 screen. Add magnesium stearate, mix and compress into desired shape on a tablet machine.

| Formulation II | Milligrams per Tablet |
|---|---|
| 3-ethyl-6-(hexafluoro-2-hydroxy-2-propyl)-1-methylquinazoline-2,4-dione | 50 |
| Lactose, U.S.P. | 191 |
| Dicalcium phosphate | 57 |
| Sodium Lauryl Sulfate | 20 |
| Polyvinylpyrrolidone | 10 |
| Water 50 ml/1000 tablets | |
| Corn starch | 20 |
| Magnesium Stearate | 2 |
| | 350 |

Mix together the stated active ingredient, lactose, dicalcium phosphate and sodium lauryl sulfate. Screen the above mixture through a No. 60 screen and granulate with an aqueous solution containing polyvinylpyrrolidone. Add additional water, if necessary, to bring powders to a pasty mass. Add corn starch and continue mixing until uniform granules are formed. Pass through a No. 10 screen, tray and dry in an oven at 40° C for 12 to 14 hours. Reduce the dried granulation through a No. 16 screen. Add magnesium stearate, mix and compress into desired shape on a tablet machine.

EXAMPLE 6

| Capsule Formulation | Milligrams per Capsule |
|---|---|
| 3-ethyl-6-(hexafluoro-2-hydroxy-2-propyl)-1-methylquinazoline-2,4-dione | 50 |
| Lactose, U.S.P. | 173 |
| Microcrystalline Cellulose | 30 |
| Sodium Lauryl Sulfate | 20 |
| Corn Starch | 25 |
| Magnesium Stearate | 2 |

| Capsule Formulation | Milligrams per Capsule |
|---|---|
| | 300 |

Mix together the stated active ingredient, lactose, microcrystalline cellulose, sodium lauryl sulfate and corn starch. Pass through a No. 80 screen. Add magnesium stearate, mix and encapsulate into the proper size two-piece gelatin capsule.

What is claimed is:

1. A quinazoline-2,4-dione of the formula:

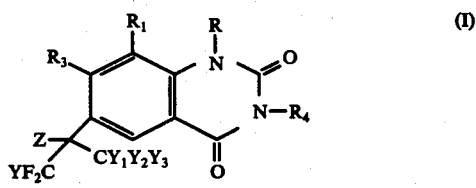

wherein

R$_4$ is a methyl, ethyl, 2-chloroethyl or 2-bromoethyl group;

R$_1$ and R$_3$ are independently hydrogen, fluorine, chlorine, bromine, lower alkyl or lower alkoxy;

Y, Y$_1$, Y$_2$ and Y$_3$ are independently hydrogen, fluorine or chlorine;

Z is hydrogen, chlorine, hydroxy or lower alkanoyloxy; and

R is hydrogen, or alkyl having 1 to 4 carbon atoms.

2. A compound according to claim 1 wherein Z is a hydroxy group.

3. A compound according to claim 2 wherein Y, Y$_1$, Y$_2$ and Y$_3$ are each independently fluorine or chlorine.

4. A compound according to claim 2 wherein Y, Y$_1$, Y$_2$ and Y$_3$ are each fluorine.

5. A compound according to claim 2 wherein R, R$_1$ and R$_3$ are hydrogen.

6. A compound according to claim 3 which is 6-(chloro-2-hydroxypentafluoro-2-propyl)-3-ethyl-1-methylquinazoline-2,4-dione.

7. A compound according to claim 4 which is 3-ethyl-6-(hexafluoro-2-hydroxy-2-propyl)quinazoline-2,4-dione.

8. A pharmaceutical composition adopted to treat hypertension comprising an oral dosage of an antihypertensively effective amount of a compound of claim 1 in a pharmaceutically acceptable diluent.

9. A composition according to claim 8 in the form of a solid oral dosage unit.

10. A composition according to claim 8 wherein said compound is 3-ethyl-6-(hexafluoro-2-hydroxy-2-propyl)quinazoline-2,4-dione.

11. A method of treating hypertension comprising orally administering to a hypertensive mammal a composition of claim 8.

12. A method according to claim 11 wherein said composition comprises 3-ethyl-6-(hexafluoro-2-hydroxy-2-propyl)quinazoline-2,4-dione.

* * * * *